(12) United States Patent
Van Wyk et al.

(10) Patent No.: US 12,147,006 B2
(45) Date of Patent: *Nov. 19, 2024

(54) ENVIRONMENTAL SENSORS AND SENSING METHODS

(71) Applicant: WAYBEYOND Limited, Auckland (NZ)

(72) Inventors: Barend Hermanus Van Wyk, Auckland (NZ); Darryn Leslie Keiller, Pukekohe (NZ); Glynn Alexander McCabe, Auckland (NZ); Jonathan Andrew Morgan, Whangaparaoa (NZ); Lee Robert Dunn, Auckland (NZ)

(73) Assignee: WAYBEYOND Limited, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 18/493,389

(22) Filed: Oct. 24, 2023

(65) Prior Publication Data

US 2024/0053507 A1    Feb. 15, 2024

Related U.S. Application Data

(63) Continuation of application No. 17/784,616, filed as application No. PCT/NZ2020/050146 on Nov. 10, 2020, now Pat. No. 11,815,652.

(30) Foreign Application Priority Data

Dec. 12, 2019   (NZ) .......................................... 760103

(51) Int. Cl.
*G01W 1/02* (2006.01)
*G01D 21/02* (2006.01)
(Continued)

(52) U.S. Cl.
CPC .............. *G01W 1/02* (2013.01); *G01D 21/02* (2013.01); *H04W 4/38* (2018.02); *H04W 84/18* (2013.01); *G01N 33/245* (2024.05)

(58) Field of Classification Search
USPC .............................................................. 702/3
See application file for complete search history.

(56) References Cited

U.S. PATENT DOCUMENTS 6,247,360 B1    6/2001   Anderson
9,319,903 B1    4/2016   Moffitt
(Continued)

FOREIGN PATENT DOCUMENTS

CN          201805769          4/2011

OTHER PUBLICATIONS

Written Opinion of the Preliminary Examining Attorney issued in PC/NZ2020/050146, dated Nov. 5, 2021 (8 pages).
(Continued)

*Primary Examiner* — Paul D Lee
(74) *Attorney, Agent, or Firm* — ARC IP Law, PC; Joseph J. Mayo

(57) ABSTRACT

Described herein is environmental sensors, sensor units, sensor systems and/or sensing methods. In particular, an agricultural or horticultural environment multi-sensor unit comprising a plurality of environmental sensors, including at least: an incident light sensor, a temperature sensor, a carbon dioxide sensor and a relative humidity sensor. The sensor unit may also comprise a wireless communication interface, the multi-sensor unit being configured to transmit data from the environmental sensors via the wireless communications interface.

19 Claims, 15 Drawing Sheets

(51) Int. Cl.
*H04W 4/38* (2018.01)
*H04W 84/18* (2009.01)
*G01N 33/24* (2006.01)

(56) References Cited

U.S. PATENT DOCUMENTS

| | | | |
|---|---|---|---|
| 10,533,892 B2* | 1/2020 | Brown | E06B 9/68 |
| 2006/0290933 A1 | 12/2006 | Holm | |
| 2009/0240353 A1* | 9/2009 | Songkakul | H04Q 9/00 |
| | | | 700/90 |
| 2014/0024313 A1 | 1/2014 | Campbell | |
| 2016/0365825 A1* | 12/2016 | Poivet | F24S 25/12 |
| 2017/0030877 A1* | 2/2017 | Miresmailli | G06N 20/00 |
| 2019/0364743 A1 | 12/2019 | Lys et al. | |
| 2020/0041316 A1 | 2/2020 | Tzur et al. | |
| 2020/0163183 A1 | 5/2020 | Lys et al. | |

OTHER PUBLICATIONS

Written Opinion of the International Searching Authority issued in PC/NZ2020/050146, dated Feb. 19, 2021 (8 pages).

International Search Report and Written Opinion issued in PC/NZ2020/050146, dated Feb. 19, 2020 (7 pages).

Bugbee, B., 'Air Temperature and Humidity—Principles of Environmental Measurement Lecture 1', ICT International and Apogee Instruments lectures that took place at the Hawkesbury Institute for the Environment campus of the Western Sydney University, Viewed on and retrieved from the Internet Feb. 18, 2021 <URL: https://www.youtube.com/watch?v=gnO4REew-1Q> Published Mar. 10, 2017 by YouTube.

Wikipedia, 'Stevenson Screen', <URL: https://web.archive.org/web/20151031114306/https://en.m.wikipedia.org/wiki/Stevenson_screen> published Oct. 31, 2015 as per Wayback Machine.

Naylor, S., 'Thermometer Screens And The Geographies Of Uniformity In Nineteenth-Century Meteorology', Royal Society Publish Notes and Records No. 73 pp. 203-221, published online Oct. 24, 2018 <URL: https://royalsocietypublishing.org/doi/pdf/10.1098/rsnr.2018.0037>.

Baranidesign, 'MeteoShield—Professional', specification sheet Jan. 1, 2017, 2 pages, viewed on and retrieved from the Internet on Nov. 4, 2021 <URL: https://static1.squarespace.com/static/597dc443914e6bed5fd30dcc/t/5bb125cd4192022ca7c6481a/1538336210290/MeteoShield+Professional+DataSheet+201809.pdf>.

* cited by examiner

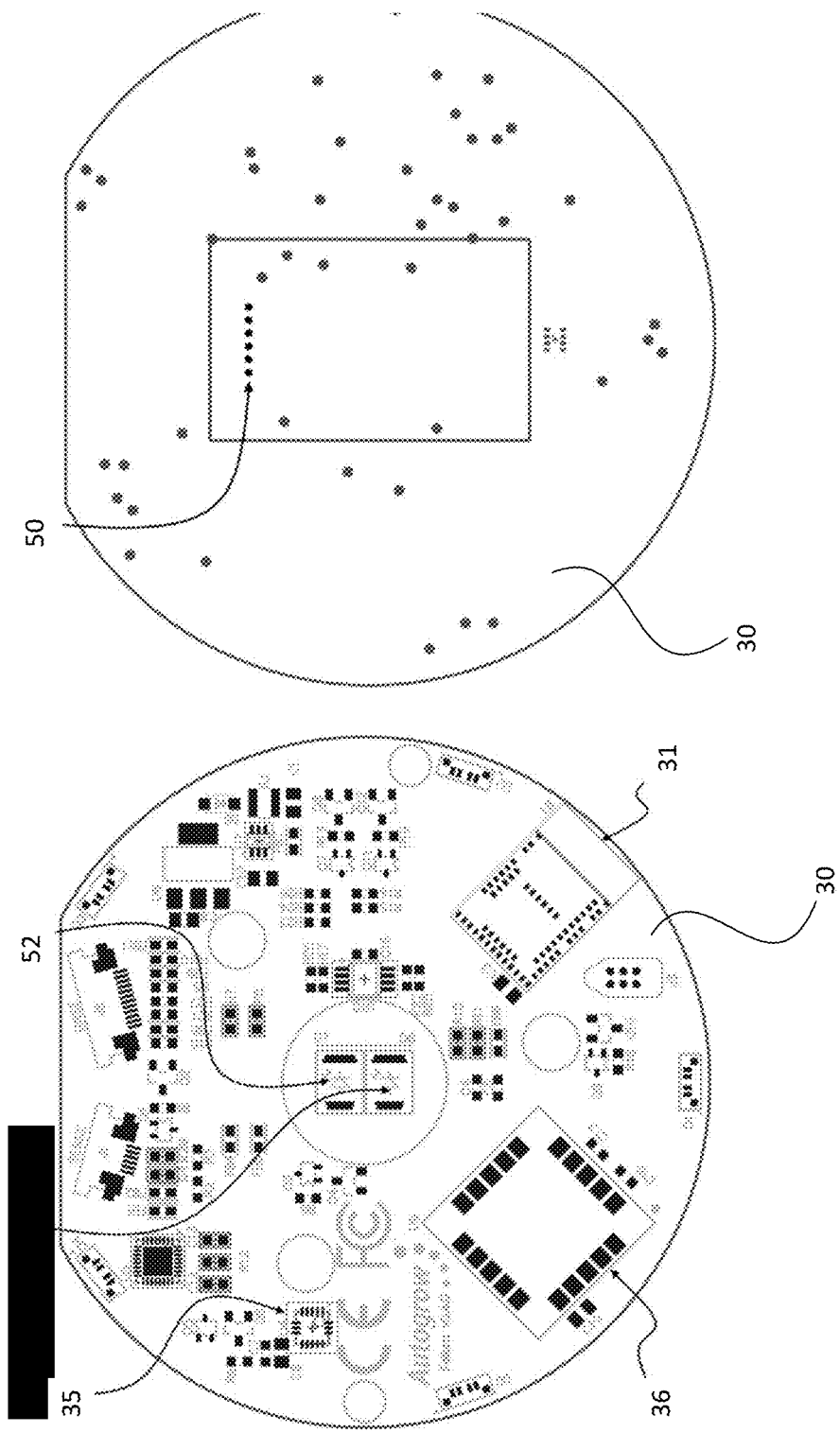

ENVIRONMENTAL SENSORS AND SENSING METHODS

This application is a continuation of U.S. Utility patent application Ser. No. 17/784,616 filed 10 Jun. 2022, which claims priority to PCT Patent Application Serial No. PCT/NZ2020/050146 filed 10 Nov. 2020, which claims priority from New Zealand patent application number 760103 filed 12 Dec. 2019, the contents of which are incorporated herein by reference.

TECHNICAL FIELD

The invention relates to environmental sensors, sensor units, sensor systems and/or sensing methods, particularly but not exclusively in agricultural or horticultural applications.

BACKGROUND ART

Environmental sensors are used in agricultural or horticultural settings in order to monitor growing conditions. Known environmental sensors include e.g. temperature, humidity and soil moisture sensors.

Typical systems use individual sensors dedicated to sensing a single environmental condition. Existing sensors also suffer from difficulty in use and/or installation, with some sensors having high power requirements and requiring physical connection to a mains power source. Some sensors are arranged for wireless communication of sensed data. However, these sensors may have limited range and communication of data in a large area typically requires the use of separate communication repeaters.

Existing individual sensors may be mounted in louvred housings in an attempt to protect the sensors while allowing accurate measurement of conditions outside the housing. However, accuracy remains problematic.

Existing sensor units are expensive and fail to provide accurate or reliable data. Existing sensor units are difficult to install and/or use and require too much power during operation.

It is an object of the invention to provide improvements in environmental sensor arrangements and/or systems and/or methods and/or in associated agricultural or horticultural systems, or at least to provide the public with a useful choice.

SUMMARY

An agricultural or horticultural environment multi-sensor unit may include a plurality of environmental sensors, including at least: an incident light sensor, a temperature sensor, a carbon dioxide sensor and a relative humidity sensor. The sensor unit may also include a wireless communication interface, the multi-sensor unit being configured to transmit data from the environmental sensors via the wireless communications interface. The sensor unit may include a battery connector for receiving power from a battery located on or in the multi-sensor unit; and a wired power connector for receiving power from an external power source.

The environmental sensors may further include a barometric pressure sensor.

The incident light sensor may be a solar irradiance sensor. The sensor unit may also include a photosynthetically active radiation sensor.

Alternatively, the incident light sensor may be a photosynthetically active radiation sensor.

The sensor unit may be configured to form a mesh network with like multi-sensor units.

The sensor unit may be configured to act as a repeater in the mesh network only when power is received from the external power source.

The sensor unit may be configured to broadcast data, wherein no pairing is required.

The sensor unit may include one or more orientation sensors.

The sensor unit may include a louvred housing in which the plurality of environmental sensors are mounted, wherein airflow through the multi-sensor unit is allowed by the louvred housing without the use of powered fans.

The sensor unit may be arranged to receive data from one or more external auxiliary sensors. A sensor assembly may include such an agricultural or horticultural environment multi-sensor unit and an external auxiliary sensor. The auxiliary sensor may be a soil moisture sensor.

An agricultural or horticultural environment multi-sensor unit may include a plurality of environmental sensors; and a louvred housing in which the plurality of environmental sensors are mounted. The environmental sensors may include at least: an incident light sensor positioned near a top surface of the housing, which is configured to allow light to enter the housing to fall on the incident light sensor; and a temperature sensor spaced from the incident light sensor and positioned such that air may flow freely through the louvred housing and over the temperature sensor.

The temperature sensor may be a combined temperature and relative humidity sensor.

The incident light sensor may be part of a first sensor assembly and the temperature sensor may be part of a second sensor assembly, each sensor assembly including one or more further environmental sensors.

The environmental sensors may include a carbon dioxide sensor and a relative humidity sensor.

The environmental sensors may include a barometric pressure sensor.

The sensor unit may include a wireless communication interface, the multi-sensor unit being configured to transmit data from the environmental sensors via the wireless communications interface.

The sensor unit may include a battery connector for receiving power from a battery located on or in the multi-sensor unit; and a wired power connector for receiving power from an external power source.

The incident light sensor may be a solar irradiance sensor. The sensor unit may include a photosynthetically active radiation sensor.

Alternatively, the incident light sensor may be a photosynthetically active radiation sensor.

The sensor unit may include one or more orientation sensors.

An agricultural or horticultural environment sensor unit may include a housing; an incident light sensor positioned within the housing; and one or more optical elements positioned on a top surface of the housing and configured such that, in use, light from a range of incidence angles will fall onto the incident light sensor.

The one or more optical elements may be arranged to disperse incident light, the dispersed incident light falling onto the incident light sensor.

The one or more optical elements may be arranged to direct incident light onto the incident light sensor.

The one or more optical elements may include one or more optical windows arranged to allow incident light through the housing.

The one or more optical elements may include one or more lenses.

An agricultural or horticultural environment sensor system may include a plurality of multi-sensor units, each including: a plurality of environmental sensors; and a louvred housing in which the plurality of environmental sensors are mounted; a wireless communications interface; wherein the multi-sensor units are configured to communicate with each other via their respective wireless communications interfaces, forming a mesh network for communication of sensor data within the controlled agricultural or horticultural environment.

The agricultural or horticultural environment sensor system may be configured for wireless communication to a gateway that supports internet connectivity.

Each sensor unit may be configured to act as a repeater in the mesh network only when power is received from an external power source.

An agricultural or horticultural system may include: a controlled growing environment; a plurality of multi-sensor units in the controlled growing environment, each according to any embodiment discussed above; one or more environmental regulation devices; and one or more controllers arranged to receive data from the multi-sensor units and to control the one or more environmental regulation devices based on the received data.

The system may be configured to control the one or more environmental regulation devices differently in different regions of the controlled growing environment based on the received data and the respective positions of the multi-sensor units in the controlled growing environment.

Each multi-sensor unit may include a position sensor.

The environmental regulation devices may include one or more of: one or more sprinklers, one or more irrigation devices, one or more humidifiers, one or more fog or mist producing devices, one or more nutrient application devices, one or more heating devices, one or more cooling devices, one or more ventilation arrangements, one or more airflow devices, one or more carbon dioxide injection devices, one or more carbon dioxide extraction devices, one or more dehumidifiers, one or more light sources, and one or more shading arrangements.

BRIEF DESCRIPTION OF THE DRAWINGS

The invention will be described by way of example only, with reference to the accompanying drawings, in which:

FIG. 11 is an upper view of a first sensor assembly according to one embodiment;

FIG. 11A is a bottom view of the first sensor assembly of FIG. 11;

DETAILED DESCRIPTION

Figure 1:
FIG. 1 is a first perspective view of a sensor unit according to one embodiment.
Figure 2:
FIG. 2 is a front view of the sensor unit of FIG. 1.

For the purposes of this specification, the term 'about' or 'approximately' and grammatical variations thereof mean a quantity, level, degree, value, number, frequency, percentage, dimension, size, amount, weight or length that varies by as much as 30, 25, 20, 15, 10, 9, 8, 7, 6, 5, 4, 3, 2, or 1% to a reference quantity, level, degree, value, number, frequency, percentage, dimension, size, amount, weight or length.

The term 'substantially' or grammatical variations thereof refers to at least about 50%, for example 75%, 85%, 95% or 98%.

The term 'comprise' and grammatical variations thereof shall have an inclusive meaning—i.e. that it will be taken to mean an inclusion of not only the listed components it directly references, but also other non-specified components or elements.

The Applicant's sensor units, systems and sensing methods may be particularly suited to application in controlled agricultural or horticultural environments. Such controlled environments may include, for example, greenhouses, indoor grow rooms, indoor farms etc.

The sensor arrangements may provide a detailed view of environmental conditions in the controlled environment.

The sensor units may include any combination of desired environmental sensors. The integration of a plurality of sensors in a single housing provides convenient gathering of multiple sensor data.

Further, the sensor units may be arranged to communicate with each other and/or with a communications gateway, in order to provide robust and convenient communication of data from the sensors. In some embodiments a mesh network may be implemented between the sensor units and the gateway. This may be achieved using any suitable wireless communications protocol. Bluetooth may be used, which may provide easy configuration using a cellphone and the range necessary to operate in a large-scale growing environment. The Bluetooth 5 protocol allows a low power usage but can still penetrate biomass. However other wireless communications technologies, such as LoRa may be used if greater range is required.

Data may be gathered and provided to a cloud-based service which provides rich visualisations and insights to the user. The sensor units may be arranged to automatically act as repeaters within the network when provided with an external power connection.

The sensor units may be arranged and/or controlled in order to limit or prevent undesirable interactions between sensors, which could impact on data accuracy. The sensor units may operate with relatively low power requirements and may be either battery powered or may receive power from an external source (e.g. mains power). Measurements of many types are therefore provided by one low powered wireless device. The measurements taken may include one or more of: temperature, relative humidity, solar irradiance, photosynthetically active radiation, air pressure, $CO_2$ concentration, and soil moisture. Other desired measurements may be added if required.

Where the sensor units include one or more incident light sensors, a lens arrangement may be used in order to pass incident light to the light sensors and in some embodiments to reduce the dependency of the sensor output on the light's angle of incidence. Further, one or more orientation sensors may be included to provide orientation data for the sensor unit. The orientation data may be used in correcting any sensor data based on known variations in the sensor data with orientation. This may be particularly useful in correcting data from the incident light sensor or sensors.

The sensors may include a carbon dioxide sensor. This sensor may be arranged to sense a concentration of carbon dioxide in the air. Infrared gas sensors may be suitable. Nondispersive infrared (NDIR) $CO_2$ sensors may be suitable. For example, a sensor from the CozIR®-LP $CO_2$ sensor range may be suitable in some embodiments.

The sensors may include one or more incident light sensors. Any suitable ambient light sensor or other photodetector may be used. Photodiode sensors may be suitable. The incident light sensors may be sensitive across a desired wavelength range. The one or more light sensors may include either or both of: a solar irradiance sensor and a photosynthetically active radiation sensor. Photosynthetically active radiation is radiation used by plants in photosynthesis (usually considered to be in the wavelength range 400 to 700 nm). In some embodiments OSRAM SFH2200 and/or SFH2240 sensors may be suitable, for example.

An optical arrangement arranged to pass incident light to the one or more incident light sensors may be included. This may be provided at the top of the sensor unit. In some embodiments the optical arrangement may include a lens structure arranged to gather light from a broad range of incidence angles and pass it to the sensor(s). This ensures that regardless of the incident angle (which may vary e.g. due to movement of the sun) the measurement is accurate. This may be further improved by ensuring that the sensor unit is level. One or more integrated orientation sensors (e.g. accelerometer and gyroscope) may be used to provide orientation information during installation, assisting the installer to level the sensor unit. The orientation sensors may also be used to monitor the angle of the product so that levelling errors can be detected.

In addition, this lens component may also provide a light pipe path from several LED lights inside the device to the outer surface of the housing to provide user feedback for installation, configuration and/or use. In some embodiments the LEDs may provide feedback during installation and then be turned off to save power. For example, in one embodiment sufficient LEDs may be provided to allow feedback to be provided that: the sensor unit is running an installation test, the test was successful, communication failure (e.g. out of range), sensor failed test (preferably with a separate indication for each sensor within the sensor unit. Any combination of LED colours, solid light, flashing light, number of LEDs etc may be used to display this information.

The sensors may include a humidity sensor. The sensor may include a temperature sensor. A single sensor measuring relative humidity and temperature may be used. For example, the Sensirion SHT35 relative humidity and temperature sensor may be suitable in some embodiments.

The sensors may include a barometric pressure sensor. For example, the Bosch BMP280 digital barometer may be suitable in some embodiments.

The sensors may include one or more position sensors. For example, any suitable GPS sensor may be used, such as the Ubox GPS-SAM-M8Q. Other positioning sensors may be used, e.g. based on local positioning systems. Further, in some embodiments users may enter sensor unit positions rather than relying on the use of a position sensor.

The sensors may include one or more orientation sensors, including e.g. 3-axis accelerometers.

The sensors may be mounted within a housing. In some embodiments a louvred housing may be used, providing airflow through the housing (and to the sensors) without the need for powered flow devices such as fans. The louvred design decouples the energy incident onto each louvre from the other louvres, making it difficult for thermal energy to travel to the inner areas of the sensor unit. This may be particularly advantageous in accurate measurement of temperature. Further, in some embodiments the temperature sensor may be protected from the influence of solar radiation which can skew the measurement upwards. This may be achieved by the louvred housing, and in addition a physical separation between the temperature sensor and at least some of the other sensors may be provided.

Combining the measurement of solar radiance and temperature into the same device poses a challenge as the light sensors must be exposed to the sun, causing local heating. The temperature sensors may be separated from the incident light sensors in order to provide accurate measurement. In particular, incident light sensor(s) may be located at the top of the sensor unit, with the temperature sensor located lower in the sensor unit (e.g. near the middle or the bottom of the sensor unit), isolating it from the effects of light heating the top of the sensor unit. The louvred design decouples the energy incident onto each plate from the other plates making it difficult for thermal energy to travel to the inner areas of the device. In addition, this structure promotes natural convection through the device allowing airflow while providing protection from water and sunlight.

The management of air flow through the sensor unit without the requirement of a separate fan unit allows the sensor unit to receive the required air across the sensors and reduces battery consumption. In some embodiments a pair of C cell batteries are expected to last up to 12 months.

External or auxiliary sensors may be connected to the sensor unit. For example, an external soil moisture sensor may be connected to the sensor unit. External sensors may communicate with the sensor unit via a wired connection, e.g. connected to an auxiliary sensor port. Alternatively, external sensors may communicate with the sensor unit over a wireless connection. External sensors may contain their own battery or external power connection, or may draw power from the sensor unit.

High quality and quantity of sensor data can be communicated via the network and uploaded to remote storage. The sensor unit can be driven by an App or any other desired interface to give one or more indications of the microclimate/environment of the greenhouse or other growing environment. Further, the data may be stored for monitoring the environment history and/or for integration into control systems. Visualisations and insights may be provided or displayed to the user. User prompts or alarms may be issued via any suitable output or display device should any of the environmental conditions satisfy an alert condition (e.g. pass a threshold, fall outside an allowed range etc). The prompts or alarms may be user-configurable via an app or other interface.

Still further, the sensor data may be used in a broader control system, in which environmental conditions are controlled in accordance with the sensor data. Environmental conditions that may be controlled include: temperature, relative humidity, ventilation, solar energy, soil moisture and the like. Ventilation systems, watering systems, heating systems, cooling systems, shading systems, lighting systems etc may all be controlled based on the sensor data. Desired values or ranges for the environmental conditions may be set by a user, e.g. via an app or other suitable interface.

The sensors within the sensor unit may be controlled to gather data at staggered times, in order to reduce the peak power requirement of the sensor unit. In particular, the carbon dioxide sensor may be operated during its own time interval as its power consumption is relatively high.

The sensor unit may be mounted in any suitable manner, and suitable fitting may be provided on the housing for pole mounting, hanging etc.

WORKING EXAMPLES

The above described apparatus, methods and uses are now described by reference to specific examples.

Example 1

FIGS. 1 to 4 show a sensor unit according to one embodiment. The sensor unit 1 includes a louvred housing 2 in which a plurality of internal environmental sensors are mounted. In general, the plurality of environmental sensors may be mounted in one or more locations within the housing 2. In the embodiment shown in FIG. 4, a first sensor assembly 3 may be mounted near the top of the housing 2 while a second sensor assembly 4 may be mounted lower in the housing 2, e.g. near the middle or bottom of the housing 2. The second sensor assembly 4 may therefore be spaced from the first sensor assembly 3.

In this embodiment, the first, upper sensor assembly 3 may include at least an incident light sensor, while the second lower sensor assembly 4 may include at least a temperature sensor. Other sensors may be located on either the first or second sensor assembly (3, 4), or may be mounted separately or in a further sensor assembly. In the embodiment shown the $CO_2$, incident light, GPS and orientation sensors are included in the first sensor assembly 3, while relative humidity/temperature and barometric pressure sensors are included in the second sensor assembly 4.

Figure 12A:
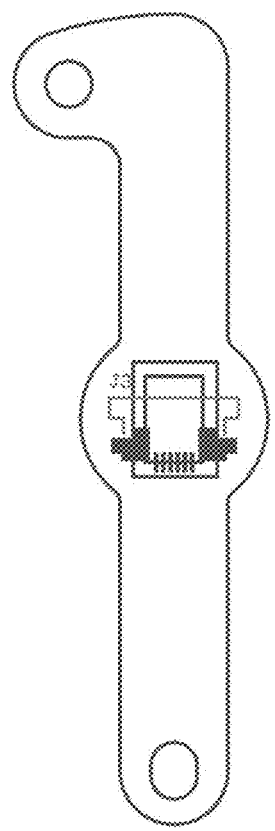
FIG. 12A is a bottom view of the sensor assembly of FIG. 12.
Figure 12:
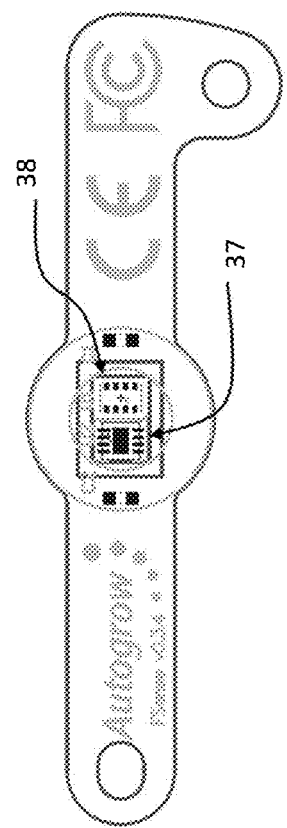
FIG. 12 is a top view of a second sensor assembly according to one embodiment.
Figure 13A:
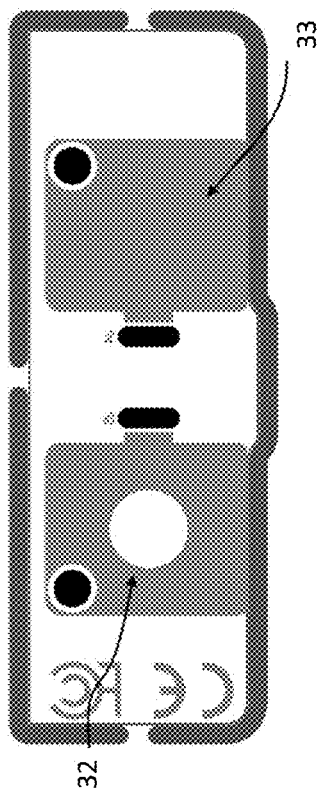
FIG. 13A is a bottom view of the assembly of FIG. 13.
Figure 13:
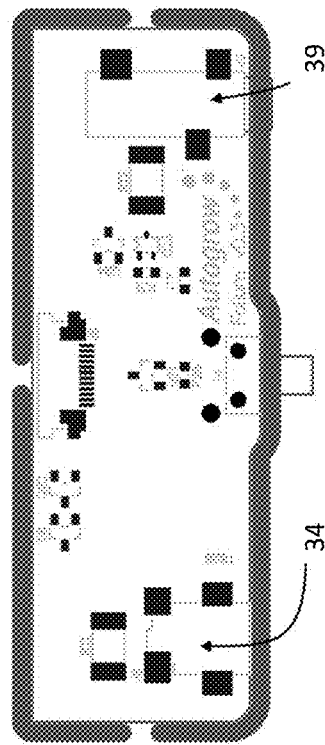
FIG. 13 is a top view of a further assembly according to one embodiment.

FIGS. 11 to 13A show circuit board assemblies that may be used in a sensor unit such as that of FIGS. 1 to 4. FIGS. 11 and 11A are top and bottom views of a first sensor assembly 3. FIGS. 12 and 12A are top and bottom views of a second sensor assembly 4. FIGS. 13 and 13A are top and bottom views of a further sensor unit assembly.

A processor mounted to the first circuit board at location 31 may communicate with the network via a wireless communications interface and gather all sensor data.

Power may be provided via battery terminals 32, 33 or through external power connector 34 located on the bottom board.

Sensor data provided by numerous sensor, which may include a $CO_2$ sensor connected to the top board using a connector 4, solar irradiation sensor mounted to the top board located at 51, photosynthetically active radiation sensor mounted to the top board located at 52, orientation sensor mounted to the top board located at 35, GPS sensor mounted to the top board located at 36, temperature and relative humidity sensor mounted to the middle board located at 37 and barometric pressure sensor mounted to the middle board located at 38. A connector 39 may be mounted to the bottom board allows for wired connection of an external auxiliary sensor or external auxiliary sensor port.

The housing 2 includes a number of louvres 6, with spaces 7 between, allowing air to flow through the interior of the housing 2 and over at least those sensors requiring airflow. In the embodiment shown, airflow is provided to the $CO_2$ sensor on the first sensor assembly 3 as well as to the sensors on the second sensor assembly 4. This provides acceptable airflow to temperature, relative humidity, air pressure and $CO_2$ concentration sensors located within the housing 2, without the need for powered flow devices such as fans.

Figure 3:
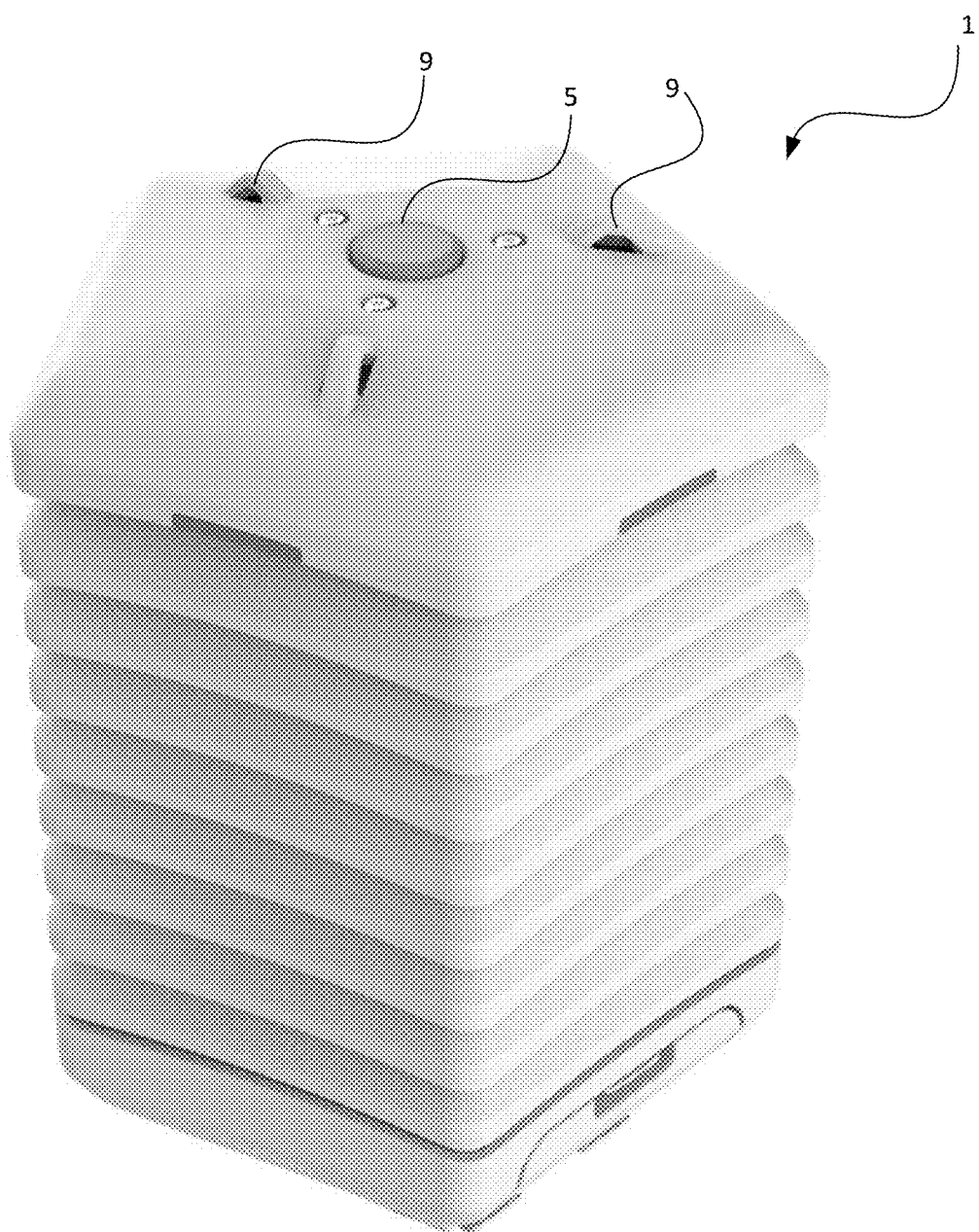
FIG. 3 is a second perspective view of the sensor unit of FIG. 1.
Figure 4:
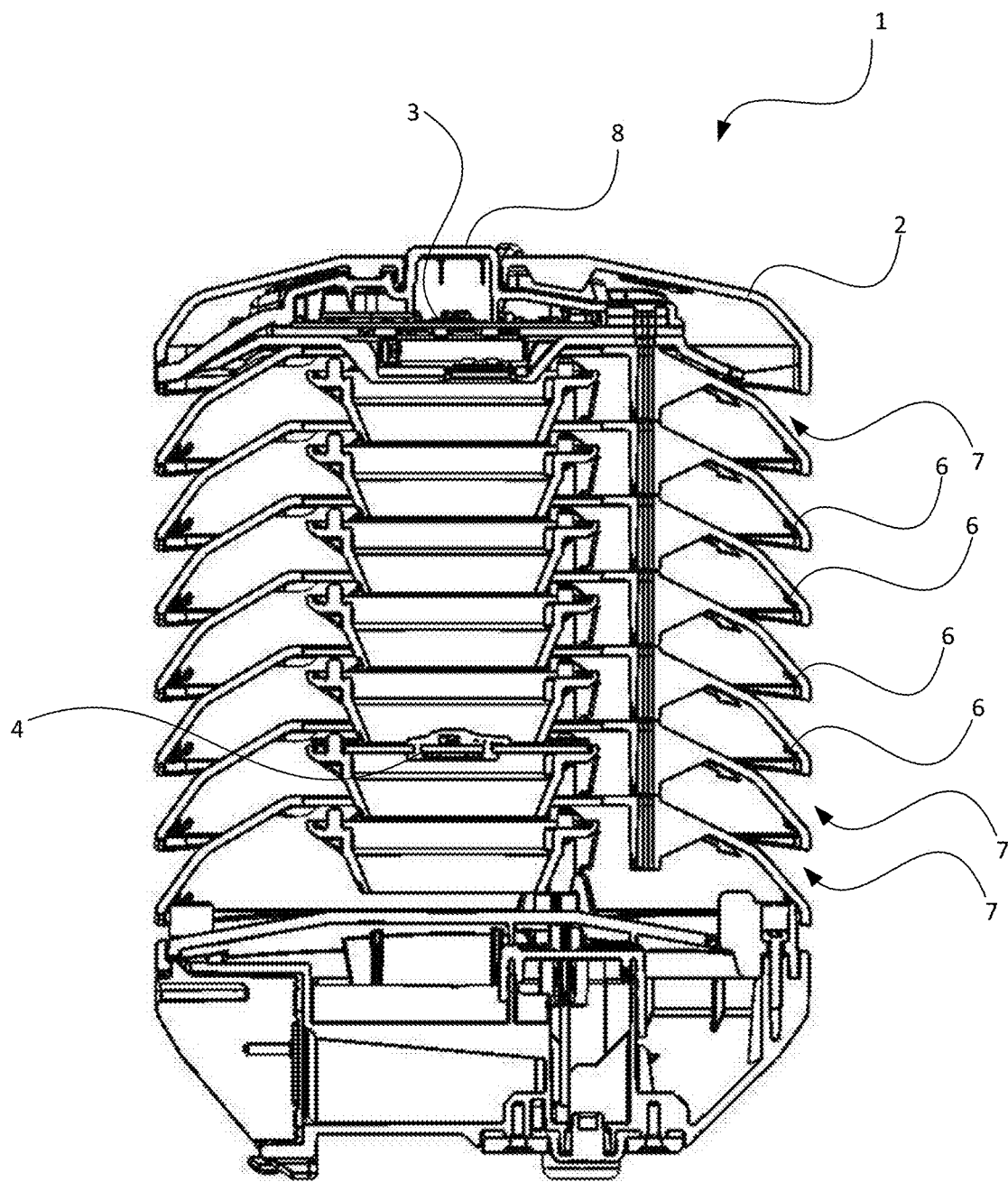
FIG. 4 is a cross-section through the sensor unit of FIG. 1.

As shown in FIGS. 3 and 4, an optical element 8 may be provided in a top surface of the housing 2, allowing incident light to pass through the housing 2 for sensing by the incident light sensor, as will be described in detail below. FIG. 3 also shows formations 9 suitable for hanging the sensor unit from a support structure.

Figure 5:
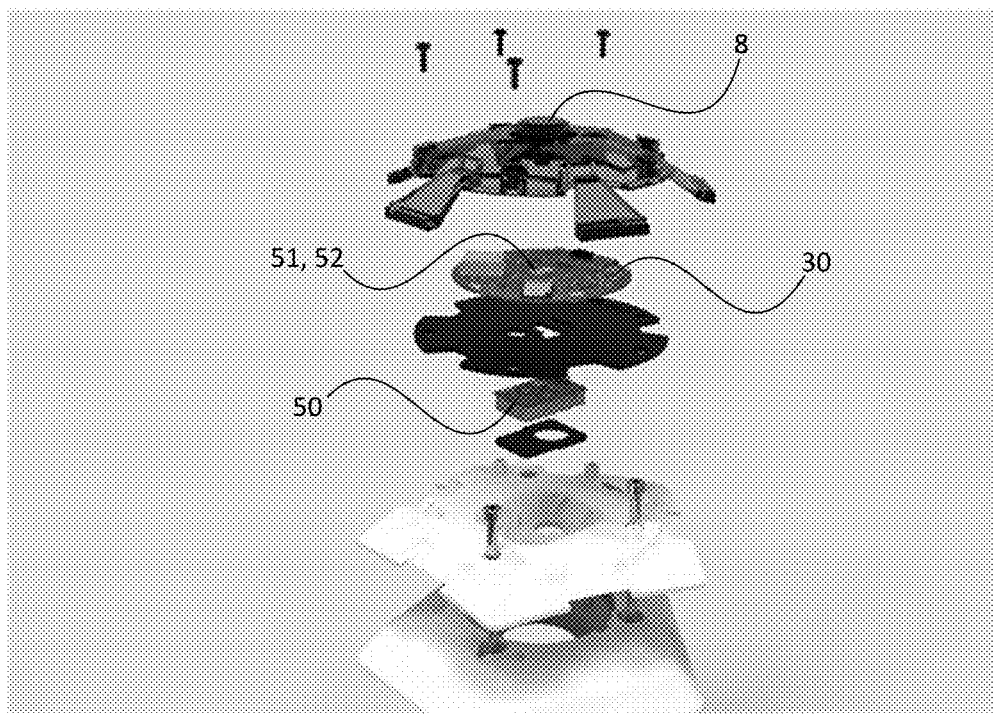
FIG. 5 is an exploded view of an upper sensor assembly, from the sensor unit of FIG. 1.
Figure 5A:
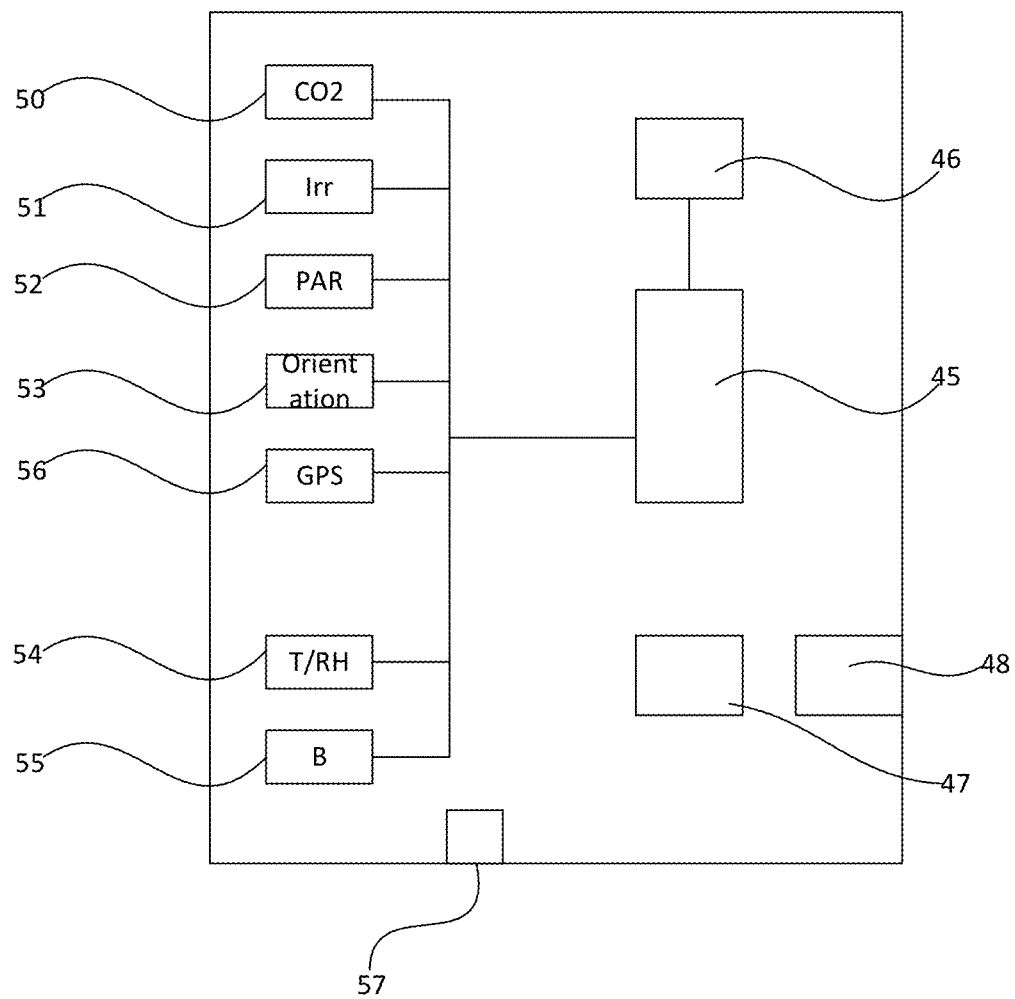
FIG. 5A is a schematic diagram showing some components of a sensor unit according to one embodiment.

FIG. 5 is an exploded view of an upper sensor assembly. A circuit board 30 may carry suitable circuitry for power and communications connections. Incident light sensors 51, 52 may be mounted to an upper surface of the circuit board 30. A $CO_2$ sensor 50 may be mounted to a bottom surface of the circuit board 30. An upper component may include one or more optical elements 8 (such as optical windows, lenses, filters, mirrors etc that are arranged to allow incident light to fall onto the incident light sensors 51, 52. The one or more optical elements 8 may disperse incident light such that dispersed incident light falls on the incident light sensors 51, 52. The one or more optical elements 8 may direct incident light onto the incident light sensors 51, 52. In some embodiments at least one of the one or more optical elements 8 may be shaped or arranged to reduce a dependence of the incident light reading on the incidence angle of the incident light. FIG. 5A is a schematic diagram illustrating some components of the sensor unit 1. A processor 45 communicates with the network via a wireless communications interface 46. A battery 47 and/or external power connector 48 provide power to the various components of the sensor unit 1. The unit 1 includes a plurality of environmental sensors, which provide data to the processor 45 and which may include a $CO_2$ sensor 50, solar irradiation sensor 51, photosynthetically active radiation sensor 52, orientation sensor 53, temperature and relative humidity sensor 54, barometric pressure sensor 55 and GPS sensor 56. A port 57 may allow for wired connection of an external auxiliary sensor. Other sensors may be included.

A reset/test switch 12 (FIG. 1) may also be included to allow a user to reset the sensor unit 1 and/or to run a test procedure.

Figure 6:
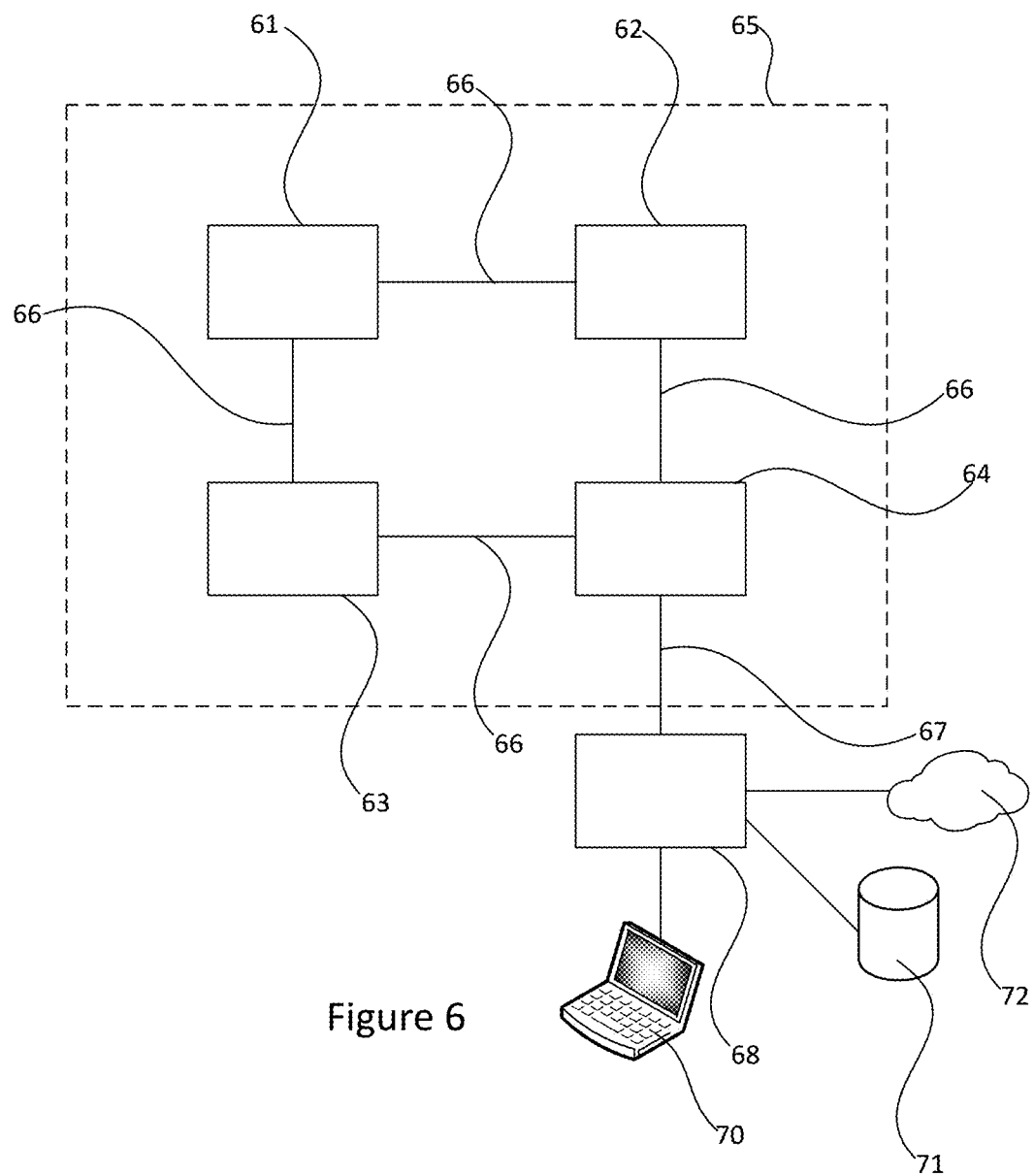
FIG. 6 is a schematic diagram illustrating a plurality of sensor units in a growing environment, and connection of the sensor units to external devices.

FIG. 6 is a schematic diagram illustrating a sensor system 60 incorporating a plurality of sensor units 61, 62, 63, 64 distributed in a controlled agricultural or horticultural environment 65. In general, any suitable number of sensor units may be used. When installed and powered, the sensor units 61, 62, 63, 64 may automatically form a mesh network via wireless communications links 66 with each other. In some embodiments all sensor units 61, 62, 63, 64 may act as full nodes/repeaters in the network. In other embodiments only sensor units that are connected to external power sources will automatically act as repeaters. The mesh network may connect via a further wireless link 67 with a gateway device 68. In some embodiments the gateway device 68 may also be part of the mesh network and/or may be incorporated into or connected by a wired connection to one of the sensor units. The gateway may connect to one or more local processors 70, databases 71 and/or to the cloud 72. A user may interact with the system through local processor 70, or may connect to the gateway 68, local processor 70, database 71 or cloud 72 using any suitable user device, including smartphones, tablets, computers or other suitable devices. Sensor data may be stored in the database 71, cloud 72 or other suitable storage.

Figure 6A:
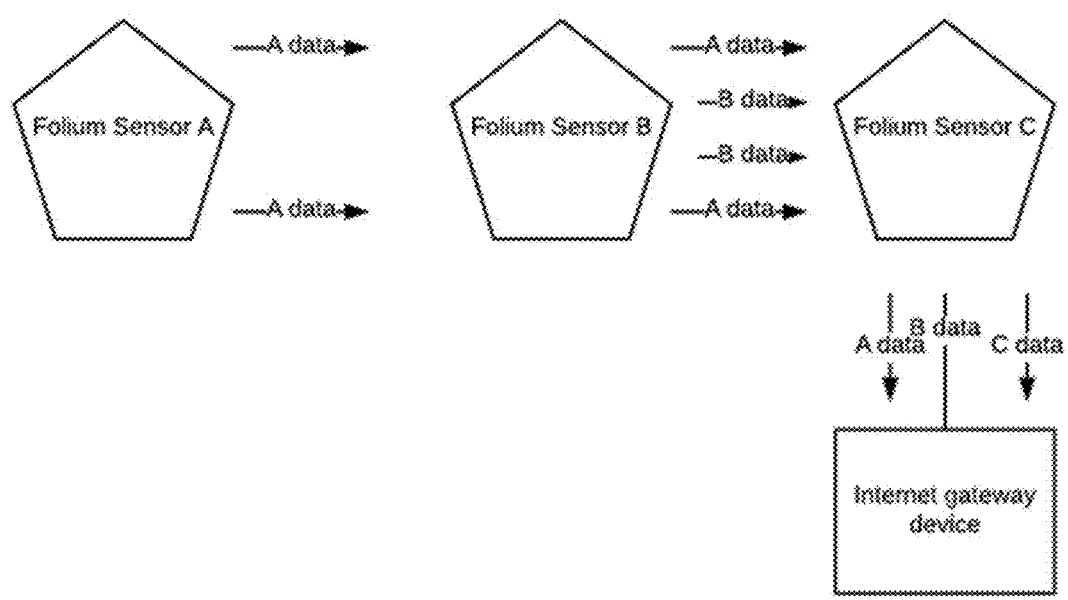
FIG. 6A is a schematic diagram illustrating communication of sensor data within a sensor network.

FIG. 6A is a schematic diagram showing how data may be transmitted through the network. A first sensor unit 61 transmits first sensor data to a second sensor unit 62. The second sensor data repeats the first sensor data and send second sensor data to a third sensor unit 64. The third sensor unit 64 repeats the first and second sensor data and sends third sensor data to the gateway device 68.

The sensors may capture data continuously or periodically. In one embodiment the sensors may measure continuously but data may be transmitted from the sensor unit periodically, e.g. every 3 to 5 minutes.

Any suitable array of sensor units may be provided within the growing space, and this may depend on the communication range, the desired spatial density of sensor data and the density of any foliage that may interfere with communication. In one embodiment Bluetooth 5 long range communications may provide a range of several hundred meters with direct line of sight, but around 40 meters through foliage. In some embodiments the spacing between sensor units may therefore be 40 meters or less.

The sensor unit array may be easily scaled for the size of a particular growing environment. Further sensor units may be added with automatic connection to the network and without the need for any pairing or manual connection process.

Figure 7:
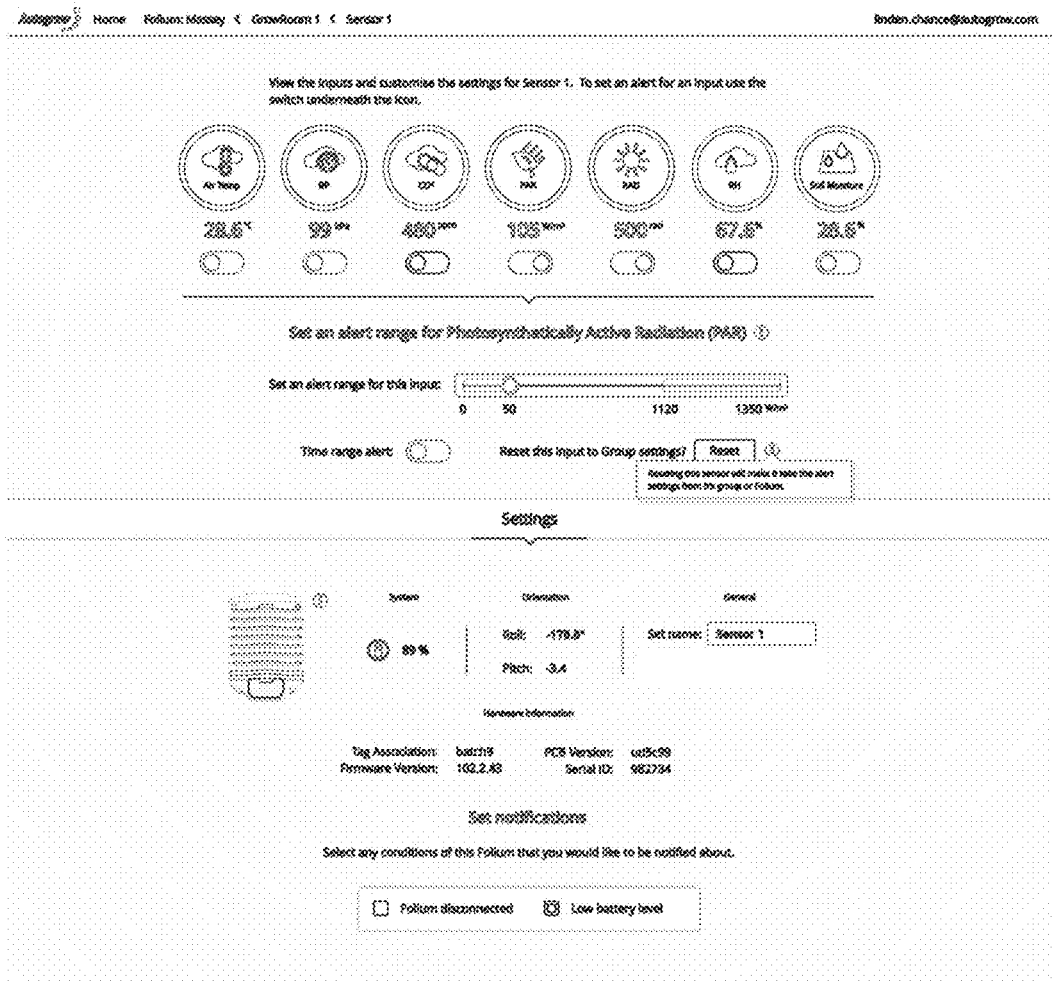
FIG. 7 illustrates display of sensor data and/or user interaction with a sensor system.
Figure 8:
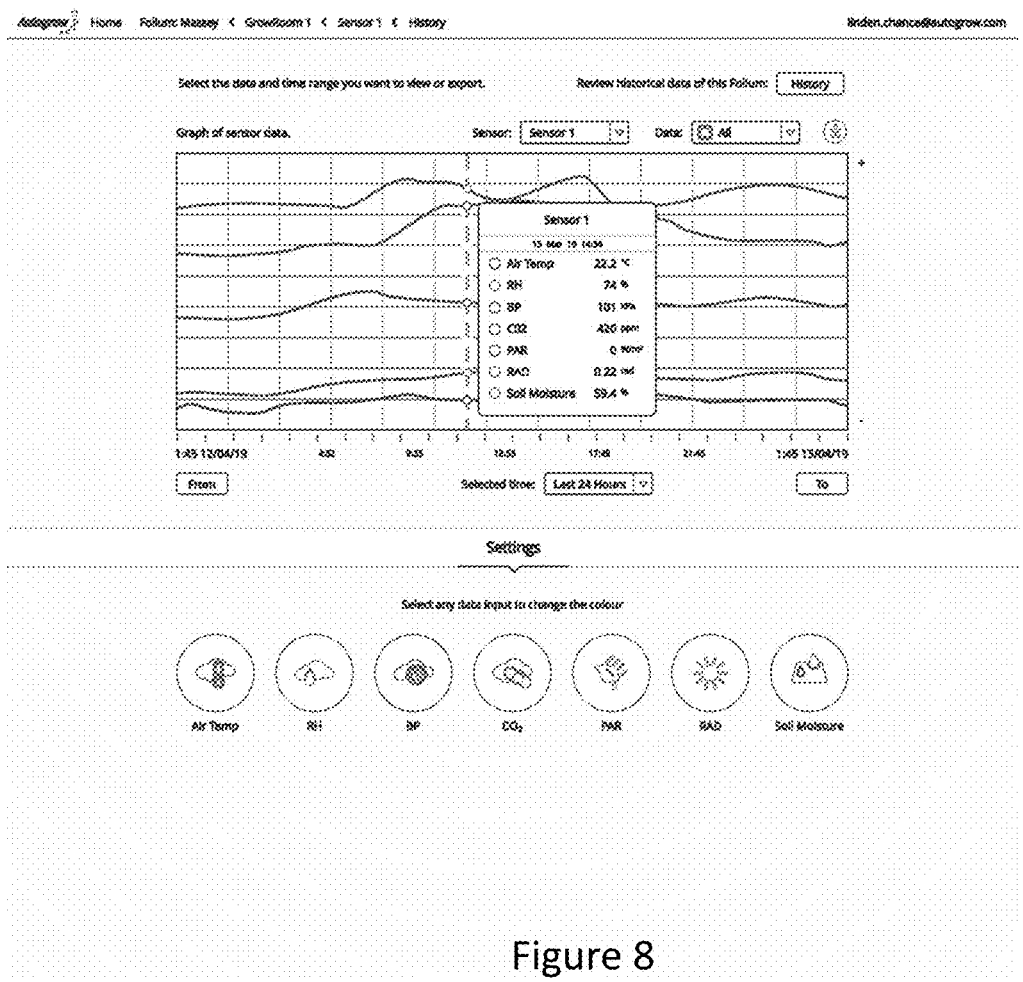
FIG. 8 further illustrates display of sensor data and/or user interaction with a sensor system.
Figure 9:
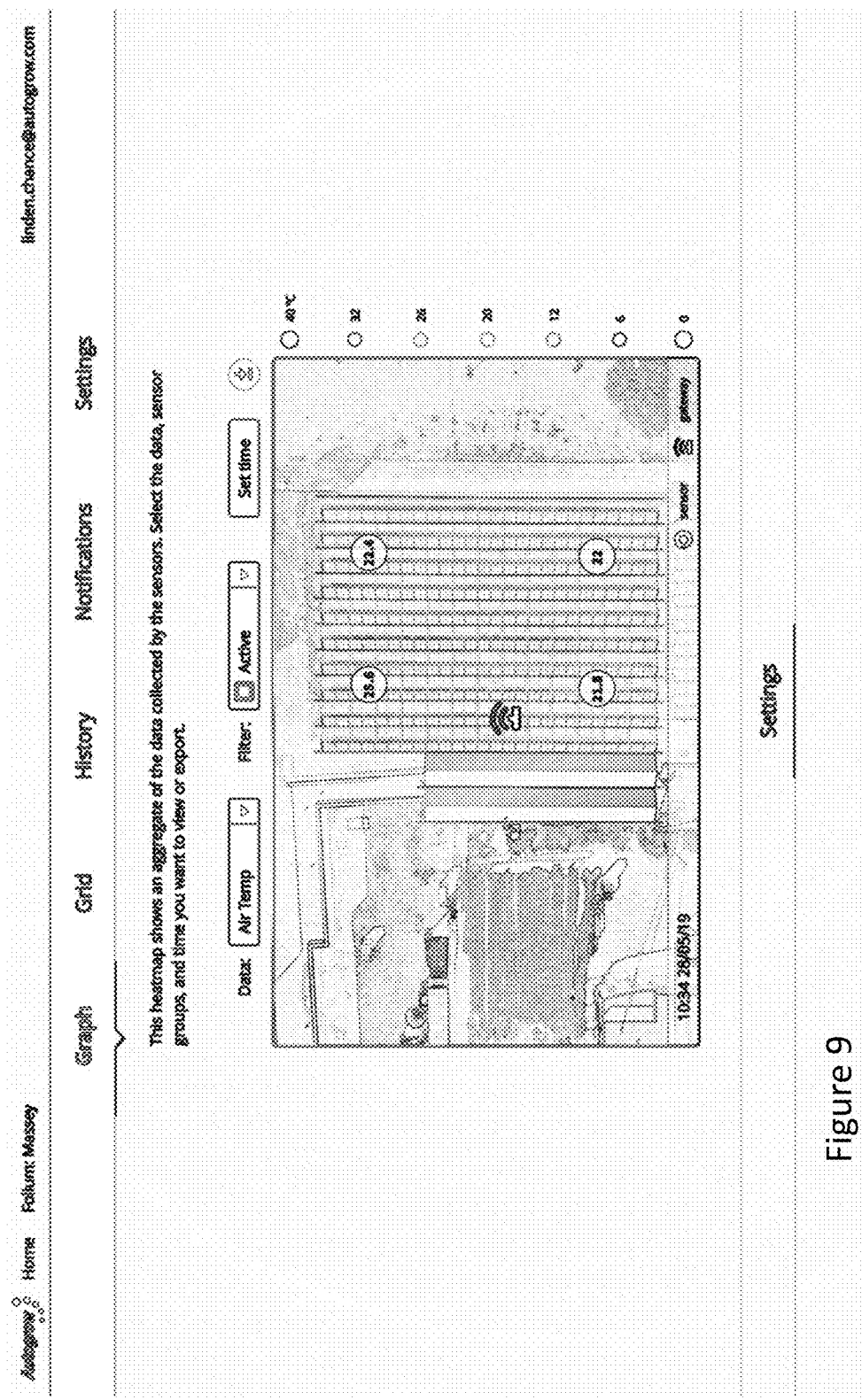
FIG. 9 illustrates display of sensor data using a heat map.
Figure 10:
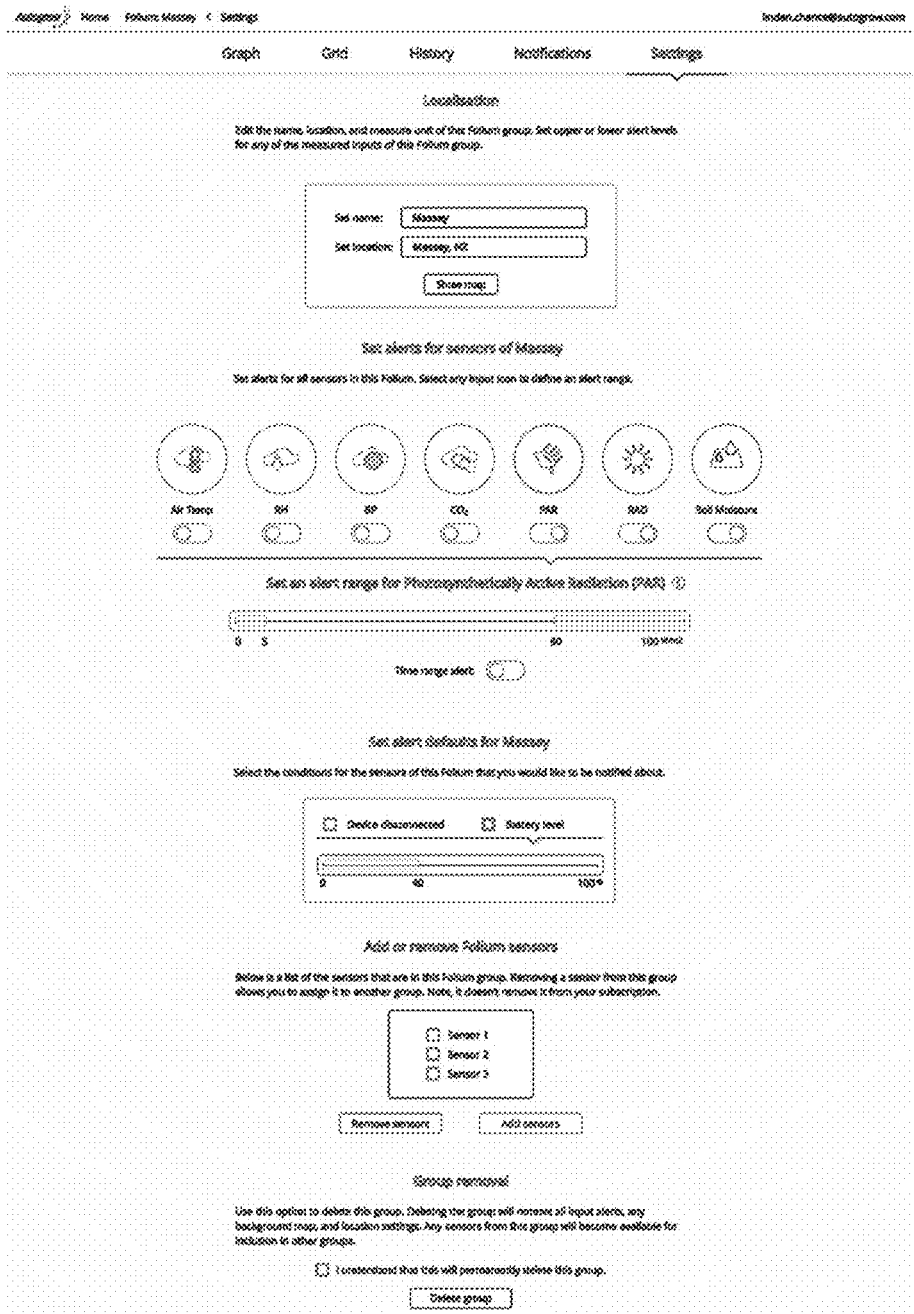
FIG. 10 further illustrates display of sensor data and/or user interaction with a sensor system.

Any desired visualisations and insights may be displayed or provided to the user/customer. For example, a detailed view of the environmental conditions present in a growing environment may be displayed. Raw data, average values, trends over time, heat maps, cumulative values over a time period etc may be displayed for each environmental condition. FIG. 7 shows a user display giving values for each environmental condition and allowing a user to set alerts for each condition. FIG. 8 shows a display of historic data for several environmental conditions against time. FIG. 9 shows a heat map for temperature in a growing environment. FIG. 10 shows a further interface allowing a user to set alerts and to add or remove sensor units.

While the present invention has been illustrated by the description of the embodiments thereof, and while the embodiments have been described in detail, it is not the intention of the Applicant to restrict or in any way limit the scope of the appended claims to such detail. Further, the above embodiments may be implemented individually, or may be combined where compatible. Additional advantages and modifications, including combinations of the above embodiments, will readily appear to those skilled in the art. Therefore, the invention in its broader aspects is not limited to the specific details, representative apparatus and methods, and illustrative examples shown and described. Accordingly, departures may be made from such details without departure from the spirit or scope of the Applicant's general inventive concept and the scope of the claims herein.

What is claimed is:

1. An agricultural or horticultural environment multi-sensor unit comprising:
   a plurality of environmental sensors;
   a wireless communication interface, wherein the agricultural or horticultural environment multi-sensor unit is configured to form a mesh network with like multi-sensor units to transmit data from the plurality of environmental sensors via the wireless communication interface;
   one or more of
      a battery connector for receiving power from a battery located on or in the agricultural or horticultural environment multi-sensor unit,
      a wired power connector for receiving power from an external power source; and
   a louvred housing in which the plurality of environmental sensors are mounted, wherein airflow through the agricultural or horticultural environment multi-sensor unit is allowed by the louvred housing without use of powered fans.

2. The agricultural or horticultural environment multi-sensor unit as claimed in claim 1, wherein the plurality of environmental sensors comprise one or more of an incident light sensor, a temperature sensor, a carbon dioxide sensor, a relative humidity sensor, a barometric pressure sensor.

3. The agricultural or horticultural environment multi-sensor unit as claimed in claim 1, wherein the plurality of environmental sensors comprise an incident light sensor, wherein the incident light sensor is a solar irradiance sensor.

4. The agricultural or horticultural environment multi-sensor unit as claimed in claim 1, wherein the plurality of environmental sensors comprise an incident light sensor, and wherein the incident light sensor is a photosynthetically active radiation sensor.

5. The agricultural or horticultural environment multi-sensor unit as claimed in claim 1, wherein the agricultural or horticultural environment multi-sensor unit is configured to broadcast data, wherein no pairing is required.

6. The agricultural or horticultural environment multi-sensor unit as claimed in claim 1, further comprising one or more orientation sensors.

7. The agricultural or horticultural environment multi-sensor unit as claimed in claim 1, wherein the agricultural or horticultural environment multi-sensor unit is arranged to receive data from one or more external auxiliary sensors.

8. The agricultural or horticultural environment multi-sensor unit as claimed in claim 1, wherein the plurality of environmental sensors comprise an incident light sensor positioned near a top surface of the louvred housing, which is configured to allow light to enter the louvred housing to fall on the incident light sensor.

9. The agricultural or horticultural environment multi-sensor unit as claimed in claim 8, wherein the plurality of environmental sensors further comprise a temperature sensor spaced from the incident light sensor and positioned such that air may flow freely through the louvred housing and over the temperature sensor.

10. The agricultural or horticultural environment multi-sensor unit as claimed in claim 9, wherein the temperature sensor is a combined temperature and relative humidity sensor.

11. The agricultural or horticultural environment multi-sensor unit as claimed in claim 9, wherein the incident light sensor is part of a first sensor assembly and the temperature sensor is part of a second sensor assembly, each sensor assembly including one or more further environmental sensors.

12. The agricultural or horticultural environment multi-sensor unit as claimed in claim 9, including a wireless communication interface, wherein the agricultural or horticultural environment multi-sensor unit is configured to transmit data from the plurality of environmental sensors via the wireless communication interface, and wherein the agricultural or horticultural environment multi-sensor unit is configured for wireless communication to a gateway that supports internet connectivity.

13. The agricultural or horticultural environment multi-sensor unit as claimed in claim 1, wherein the agricultural or horticultural environment multi-sensor unit is configured to act as a repeater in the mesh network only when said power is received from the external power source.

14. A sensor assembly comprising:
an agricultural or horticultural environment multi-sensor unit, wherein said agricultural or horticultural environment multi-sensor unit comprises
a plurality of environmental sensors, including at least an incident light sensor, a temperature sensor, a carbon dioxide sensor and a relative humidity sensor;
a wireless communication interface, wherein the agricultural or horticultural environment multi-sensor unit is configured to form a mesh network with like multi-sensor units to transmit data from the plurality of environmental sensors via the wireless communication interface;
one or more of
a battery connector for receiving power from a battery located on or in the agricultural or horticultural environment multi-sensor unit,
a wired power connector for receiving power from an external power source; and
a louvred housing in which the plurality of environmental sensors are mounted, wherein airflow through the agricultural or horticultural environment multi-sensor unit is allowed by the louvred housing without use of powered fans; and
an external auxiliary sensor, wherein said agricultural or horticultural environment multi-sensor unit is arranged to receive data from the external auxiliary sensor.

15. The sensor assembly as claimed in claim 14, wherein the external auxiliary sensor is a soil moisture sensor.

16. An agricultural or horticultural system, comprising:
a controlled growing environment;
a plurality of multi-sensor units in the controlled growing environment, each multi-sensor unit of the plurality of multi-sensor units comprising
a plurality of environmental sensors, including at least an incident light sensor, a temperature sensor, a carbon dioxide sensor and a relative humidity sensor;
a wireless communication interface, wherein the each multi-sensor unit is configured to form a mesh network with like multi-sensor units to transmit data from the plurality of environmental sensors via the wireless communication interface;
a louvred housing in which the plurality of environmental sensors are mounted, wherein airflow through the each multi-sensor unit is allowed by the louvred housing without use of powered fans;
one or more environmental regulation devices; and
one or more controllers arranged to receive data transmitted from the plurality of multi-sensor units and to control the one or more environmental regulation devices based on the data that is received.

17. The agricultural or horticultural system as claimed in claim 16, configured to control the one or more environmental regulation devices differently in different regions of the controlled growing environment based on the data that is received and respective positions of the plurality of multi-sensor units in the controlled growing environment.

18. The agricultural or horticultural system as claimed in claim 16, wherein each multi-sensor unit further comprises a position sensor.

19. The agricultural or horticultural system as claimed in claim 16, wherein the one or more environmental regulation devices include one or more of: one or more sprinklers, one or more irrigation devices, one or more humidifiers, one or more fog or mist producing devices, one or more nutrient application devices, one or more heating devices, one or more cooling devices, one or more ventilation arrangements, one or more airflow devices, one or more carbon dioxide injection devices, one or more carbon dioxide extraction devices, one or more dehumidifiers, one or more light sources, and one or more shading arrangements.

* * * * *